US011728147B2

(12) United States Patent
Pamukcu et al.

(10) Patent No.: US 11,728,147 B2
(45) Date of Patent: Aug. 15, 2023

(54) QUANTIFICATION OF PREVIOUSLY UNDETECTABLE QUANTITIES

(71) Applicant: Definitek, Inc., Sunnyvale, CA (US)

(72) Inventors: Mehmet Pamukcu, Sunnyvale, CA (US); Howard M. Kingston, Pittsburgh, PA (US)

(73) Assignee: Definitek, Inc., Sunnyvale, CA (US)

(*) Notice: Subject to any disclaimer, the term of this patent is extended or adjusted under 35 U.S.C. 154(b) by 71 days.

(21) Appl. No.: 17/502,906

(22) Filed: Oct. 15, 2021

(65) Prior Publication Data
US 2022/0148868 A1 May 12, 2022

Related U.S. Application Data

(60) Provisional application No. 63/093,881, filed on Oct. 20, 2020.

(51) Int. Cl.
*H01J 49/00* (2006.01)
*G01N 33/96* (2006.01)

(52) U.S. Cl.
CPC .......... *H01J 49/0031* (2013.01); *G01N 33/96* (2013.01)

(58) Field of Classification Search
CPC ............... G01N 33/6848; G01N 33/96; G01N 33/6893; G01N 2458/15; H01J 49/0031
See application file for complete search history.

(56) References Cited

U.S. PATENT DOCUMENTS 6,974,951 B1 * 12/2005 Kingston ............ H01J 49/0031
250/281

FOREIGN PATENT DOCUMENTS

CN     112805299 A  *  5/2021  ............. C07K 16/18

* cited by examiner

*Primary Examiner* — David E Smith
*Assistant Examiner* — Hsien C Tsai
(74) *Attorney, Agent, or Firm* — Barbara E. Johnson, Esq.

(57) ABSTRACT

The present invention centers upon a novel "molecular amplification spike," which is an admixture of two components, namely, an aliquot of a quantity of a molecule, composition, compound or element of interest (an "analyte") in its natural isotopic state and an aliquot of an isotopically enriched form of the same molecule, composition, compound or element. The molecular amplification spike contains 20% natural-abundance isotope, balance enriched isotope. The molecular amplification spike may optionally contain more than 20% natural-abundance isotope, with concomitantly reduced balance of enriched isotope. Such an admixed spike, when added to a sample prior to mass spectrometric analysis of that sample, creates new and significantly improved percentage of errors and quantification or confirmation of the absence of the molecule, composition, compound or element of interest in the sample.

10 Claims, 1 Drawing Sheet

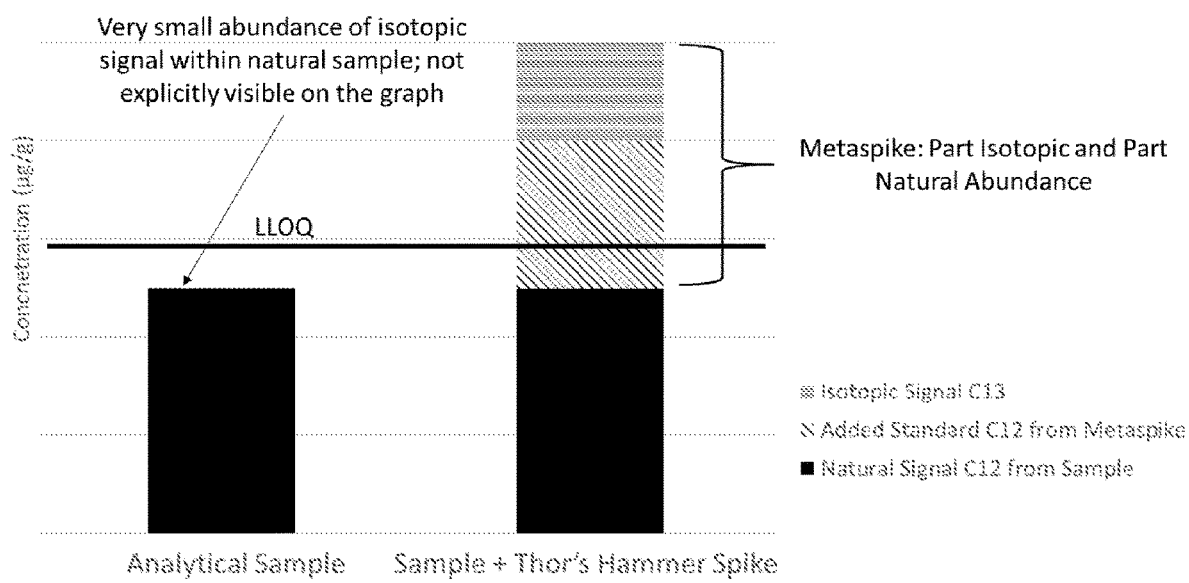

QUANTIFICATION OF PREVIOUSLY UNDETECTABLE QUANTITIES

CROSS-REFERENCE TO RELATED APPLICATION

This patent application is a nonprovisional based on U.S. Provisional Patent Application No. 63/093,881, filed 20 Oct. 2020, to which priority is claimed and which is incorporated herein by reference.

BACKGROUND OF THE INVENTION

Field of the Invention

The present technology uses a novel molecular amplification spike, in the context of mass spectrometry, to make it possible for the first time to quantify molecules, compositions, compounds or elements of interest—that have previously been present in amounts below the LLOQ, or (prior) Lower Level of Quantification, sometimes referred to as limit of quantification (LOQ) in a sample of medical, biological, environmental, industrial or any other origin, requiring evaluation. The human body has a concentration gradient of approximately ten to the 23 in concentration differences in molecule concentration and many of the biomarkers are in the lower concentration that are below the LLOQ of the mass spectrometers.

Mass spectrometry still has inherent limitations, despite its versatility and popularity in both research and medical laboratories. Currently used quantification methods that relies on calibration curves not work well with mass spectrometry at or near trace-level analysis close to the LLOQ, because inherent limitations of mass spectrometry are widened in a compounded manner. Indeed, the use of mass spectrometry in the life sciences for medical applications has been limited, heretofore, due to quantification difficulties and often unpredictable variations of percent errors. Even when the same mass spectrometer is used to analyze a sample at different time intervals, or different personnel use the same mass spectrometer to analyze the same sample, obtaining reliable mass spectrometry results can be elusive—even to this day. Mass spectrometers sensitivity related to the LOQ is based on the type, tune, physics of operational conditions and ionization methods.

Alongside the challenges posed by mass spectrometry limitations, chain of custody (sample collection, transportation, storage and evaluation) also frequently contributes to inconsistent results for many reasons, including sample instability and errors in sample preparation. Medical diagnostics, for example, continues to head in the "molecular biomarker" direction, and for good reason—biomarkers (and imaging) direct medical treatment to a degree unprecedented in history. For medical sample collection, however, there are often legal and practical barriers. For instance, a blood sample may need to be transported across geographic boundaries, while at the same time there are laws and regulations that prevent such shipments internationally and even, sometimes, locally. Apart from laws and rules, there are practical limits on shipping of viable biological specimens, such as blood and tissue samples, including but not limited to weather issues, ambient temperature incompatibilities, shipping delays, packaging concerns, and avoidance of specimen deterioration due to transport time. Many populations in remote locations need medical sample evaluation despite the local unavailability of refrigeration, fast shipping, and so forth—yet the children or other patients in such locations are in need of competent diagnostics notwithstanding these infrastructure challenges. The challenges are not just medical—industrial, environmental, and other types of samples can require evaluation on either a routine or an emergency basis, and such samples need to get from their source to their testing laboratory, without deterioration. Mass spectrometry field has long sought for methodology innovation, to identify—and quantify—constituents that are present in any sample in heretofore unquantifiable, even undetectable amounts AND can use easily transported, stable, small samples to avoid the hurdles of sample deterioration caused by conditions associated with chain of custody.

According, a need remains to solve two problems at once: the ability of mass spectrometry to quantify heretofore undetectable molecules, compositions, compounds or elements in a biological, environmental, industrial or other sample needing quantification, AND at the same time, to streamline the sample collection, stabilization and transport of a minimal amount of material to be analyzed. Ideally, such a technology would be able to quantify amounts two orders of magnitude lower than previously achievable sensitivity and quantification possible with prior art mass spectrometry.

BRIEF DESCRIPTION OF THE FIGURES

FIG. 1 is a bar graph which shows how the invention, colloquially referred to as "Thor's Hammer," is able to provide signal amplification using a METASPIKE™ molecular amplification spike addition to a sample prior to mass spectrometry analysis.

SUMMARY OF THE INVENTION

In order to meet this need, the present invention collects one or more (generally small) samples containing one or more of molecules, compositions, compounds or elements known or suspected to be present in amounts less than the previously accepted LLOQ (Lower Limit of Quantification). The sample(s) are collected in a way that renders the sample size either small (10-30 microliters) or stabilized (such as dried liquid on a carrier, such as simple blood spots on a card). These small samples are thereafter analyzed in a mass spectrometer after they are treated with (contacted by) a molecular amplification spike. The molecular amplification spike is an admixture of two components, namely, an aliquot of a quantity of a molecule, composition, compound or element to be quantified in its natural isotopic state, admixed with an aliquot of an isotopically enriched form of the same molecule, composition, compound or element. The molecular amplification spike contains 20% natural isotope, balance enriched isotope. The molecular amplification spike may optionally contain more than 20% natural isotope, with concomitantly reduced balance of enriched isotope. Typically but not necessarily, the natural isotope is present in the molecular amplification spike at no more than 90% natural isotope, more preferably no more than 70%. When the sample to be analyzed is contacted with a quantity of the molecular amplification spike prior to mass spectrometry of the sample, the combination of the amplification provided by the natural isotope, plus the isotopic shift tracking possible with the presence of the isotopically enriched portion of the spike, both enables mass spectrometry signal generation and also reverse calculation of the initial quantity of the natural isotope originally present in the collected sample. Species that are fragile and shift from one to another during measurement are addressed in Speciated Isotope Dilution Mass Spectrometry (SIDMS). SIDMS also benefits from this invention as important fragile species such as drugs and biomarkers are critically assessed quantitatively at near or at the LOQ of mass spectrometers—so the same premixed molecular amplification spikes of the present invention may be used in SIDMS also. (Instability of the substance (analyte) is where the present molecular amplification spike makes SIDMS "shine even brighter than ever," because SIDMS already allows the tracking of the interconversions between two variants simultaneously, and analysis in a single test, to report the most accurate and precise concentrations of both the analyte and the variant in the sample right before collection—which is when the interconversions would have begun.) Reverse calculations are well known to those skilled in the art of Isotope Dilution Mass Spectrometry and its analogues, and can easily be automated—but no one before now has ever thought to add natural isotope to an isotopically enriched spike to create the present molecular amplification spike. Due to the power of the molecular amplification spike addition, very small samples (10-30 microliters) either as liquids, or as dried spots on a carrier (such as a simple cellulose card, inert polymer or any solid matrix of any type) obviate the need for expensive shipping of significantly greater liquid masses and weights of otherwise biohazardous materials restricted by state, federal and international regulations, or susceptible to weather, temperature or time degradation.

DETAILED DESCRIPTION OF THE INVENTION

In the analytical world, there are a myriad of elusive molecules, compositions, compounds and elements whose presence need not only to be discovered and verified—but also to be quantified. These include, without limitation, suspected food or drug contaminants, toxicants, blood or body fluid metabolites, drug residues including residues of substances of abuse, degradation contaminants in industrial lubricants, air pollutants from industry or agricultural pollution from pesticides—the list is endless. When these substances are elusive, that is, present in small but devastatingly significant amounts, this invention is directed toward quantifying them! With the techniques described herein, for the first time, molecules, compositions, compounds and elements of all sort and types may be identified and quantified from all manner of samples—medical, biological, environmental, industrial, or any other source of concerned investigation.

An initial problem addressed with the present invention was—identifying and quantifying low levels of curcuminoids in cerebral spinal fluid. The need to do this arose because neurologist MD's were studying these turmeric extracts that could pass through the blood/brain barrier, for the purposes of research into treatment of Alzheimer's Disease, to try to find bioreactive agents that might stop demyelination and the formation of the troublesome amyloid plaques that are the main culprits in Alzheimer's Disease. In investigating curcuminoids, the research physicians could see that several forms of curcumin were indeed present in the cerebrospinal fluid, but no one could quantify how much was there. By using a molecular amplification spike containing 20% natural isotope of curcumin, balance isotopically enriched curcumins, and the methods of this patent specification, it is now possible to quantify curcuminoids in cerebrospinal fluid—despite their low concentration. Quantifying amounts of curcumins, or anything else, in cerebrospinal fluid is a vital measurement that is needed to determine the effective level of dosing for a substance intended to pass through the blood/brain barrier and not too high to create adverse effects.

When molecules, compositions, compounds or elements are present above the LLOQ, generally speaking, prior or known processes for quantifying them may be used, such as Isotope Dilution Mass Spectrometry, Speciated Isotope Dilution Mass Spectrometry, and so forth. Various prior art techniques are disclosed and explained in these inventors' own prior patents, including but not limited to U.S. Pat. Nos. 6,790,673, 8,383,420, 9,869,684, and 10,962,556. For the purpose of the present technology, however, the inventors describe and claim the use of a molecular amplification spike to effect identification and quantification of molecules, compositions, compounds and elements that were present below the previous LLOQ, as a particular focus of the present technology and the problems it can solve. The aforementioned patents do NOT address, even implicitly, any way to assess and quantify substituents present below the LLOQ as it existed prior to the present invention.

In addition to probing, identifying and quantifying molecules, compositions, compounds and elements that were previously present below the LLOQ, it is also important to be able to find low-concentration molecules, compositions, compounds and elements before they convert into their variant molecules. Keeping track of the reduced glutathione (native form) versus oxidized glutathione is important, and also various elusive substances such as heroin must be found and quantified before they transform—heroin in a blood or fluid sample often transforms quickly to morphine and can no longer be identified as heroin, for example. Other substances that convert easily, and therefore need to be assessed quickly, include without limitation, 6-methamphetamine, cocaine, benzoylecgonine, methadone, 2-ethylidene-1,5-dimethyl-3,3-diphenylpyrrolidine (EDDP), buprenorphine, norbuprenorphine, gabapentin, celecoxib, naloxone, normaloxone, noroxymorphone, fentanyl, norfentanyl, oxycodone, noroxycodone, tetrahydrocannabinol, cannabidiol and loperamide. By the same token, persistent organic pollutants need to be identified before they convert to other forms, as well, in an environmental sample for analysis. These pollutants include, without limitation, naphthalene, acenaphthene, fluorene, phenanthrene, pyrene, benz[a]anthracene, chrysene, benzo[b]fluoranthene, benzo[a]pyrene, indeno[1,2,3-cd]pyrene, dibenz[a.h]anthracene, cichlorodiphenyltrichloroethane, dichlorodiphenyldichloroethylene, and dichlorodiphenyldichloroethane. Arguably higher priority substances that must be identified and quantified are harmful pollutants and toxicants in foods and drugs, such as without limitation, mercury (in its various forms), polydimethylsiloxane (PDMS), chromium, lead, and arsenic—and the list of potential dietary contaminants is in the thousands. A serious and persistent health concern pervades the entire nutritional supplement industry, as consumers and manufacturers alike want to know what if any contaminants are present in what they otherwise hope are wholesome vitamin and mineral, herbal, and other nutritional supplements. Various homeland security initiatives require quantification of fugitive agents and chemical weapons of mass destruction. Authentication of products, valuable objects, legal documents requires unbreakable molecular coding that must be assessed in tiny-quantity levels in order to deter forgery. As illuminated here, therefore, the list of materials for which low-level incidence, and quantification, are needed—is literally endless.

The key in identifying and quantifying otherwise elusively low levels of molecules, compositions, compounds and elements lies in, therefore, the ability of the present molecular amplification spike to make detectable (and quantifiable), by mass spectrometry, substances whose signal would otherwise be subsumed within the "noise" level of the output of the spectrometry, without the amplification spike. This molecular amplification spike, or METASPIKE™, is the inventive gravamen in which a percentage of natural-abundance isotope is combined, with an enriched isotope, to make a hybrid spike (with a spike's being a material of addition) containing both the natural-abundance isotope and an enriched isotope, of the same substance for which identification and quantification is sought. As described above, the present invention collects one or more small samples containing one or more of molecules, compositions, compounds or elements known or suspected to be present in amounts less than the previously accepted LLOQ. The sample(s) are collected in a way that renders the sample size either small (10-30 microliters) and/or stabilized (for example dried liquid on a carrier, such as simple blood spots on a filter encased in a card). These small samples are thereafter analyzed in a mass spectrometer after they are treated with (contacted by) a molecular amplification spike. The molecular amplification spike is an admixture of two components, namely, an aliquot of a quantity of a molecule, composition, compound or element to be quantified in its natural isotopic state, admixed with an isotopically enriched form of the same molecule, composition, compound or element. To achieve clinically acceptable precision and quantification, the molecular amplification spike contains 20% natural isotope, balance isotopically enriched isotope, of the same substance of interest. The molecular amplification spike may optionally contain more than 20% natural isotope, with concomitantly reduced balance of isotopically enriched isotope. (For the purposes of the invention, "containing 20%" will be true of a real-world spike that contains, for example, 22%—of course it also empirically contains 20% of the naturally occuring isotope.) Typically but not necessarily, the natural isotope is present in the molecular amplification spike at no more than 90% natural isotope. When the sample to be analyzed is contacted and equilibrated with a quantity of the molecular amplification spike prior to mass spectrometry of the sample, the combination of the amplification provided by the natural isotope—plus the isotopic shift tracking possible with the presence of the isotopically enriched portion of the spike—both enables mass spectrometry signal generation and also reverse calculation of the initial quantity of the molecules, compositions, compounds or elements originally present in the collected sample. These reverse calculations are well known to those skilled in the art of Isotopic Dilution Mass Spectrometry, and can easily be automated—but no one before now has ever thought to add natural isotope to an isotopically enriched spike to create a molecular amplification spike that can be optimized to achieve the desired level of quantitation below the LLOQ. Due to the power of the molecular amplification spike addition, very small samples (10-30 microliters) either as liquids or as dried spots on a carrier (such as a simple cellulosic fiber, inert polymer or solid matrix of any type) obviate the need for expensive shipping of significantly greater liquid masses and weights of otherwise biohazardous materials restricted by state, federal and international regulations, or susceptible to weather, temperature or time degradation. In practice, one should bear in mind that the use of a quantitative dried blood spot card (DBS) generally reduces the signal of the sample and spike by five times, so without the present molecular amplification spike, for example, a 10 to 20 microliter (uL) dried blood spot would not be quantifiable for GSSG (oxidized glutathione) and MMA (methylmalonic acid), each having an approximate LLOQ of 42 ug/g and 12 ug/g (micrograms per gram) respectively. These quantified measurements were just above the LOQ on an Agilent 6460 triple quadrupole mass spectrometer using electrospray jet stream. The use of the present molecular amplification spike with the dried blood spot cards is particularly important because, without the present admixed spike, many dried blood spot constituents of interest are simply below the level of LLOQ, resulting wide variance and large percent errors. With the present spike the practical and economic benefits of collecting blood samples as dried blood spots on a card, rather than in tubes, is enormous and potentially transformational.

Automation of evaluation of samples, in the partially analogous field of Isotope Dilution Mass Spectrometry (IDMS), is well known in the art. The prior art, IDMS, is based on the reliable phenomenon that the majority of elements have two or more stable isotopes whose abundance in nature remains constant. When a known amount of an enriched stable isotope is added to a sample to be analyzed, this reliable "remains constant" phenomenon will cause the proportion of isotopes to adjust, after a brief period of equilibration. After equilibration, the ratio between or among the isotopes can then be measured by mass spectrometry and, working backwards, it is possible to determine the original concentration of the element (or other substance) in the sample, by mathematically "backing out" the isotopic shift that occurred during equilibration. Because spectrometers and computers have been able "to talk" to one another for decades, feedback mechanisms "to run" (in the mass spectrometer) adjusted samples under adjusted reaction conditions, over time, is already a mature technology. In the present invention, because it is known that by adding a 20% natural-abundance isotope/remainder isotopically enriched spike to a sample will enhance the signal generation of the "unknown analyte" sought to be identified and quantified, it is already well within the skill of the art to create automated seriatim sample testing in which successive samples are analyzed with spikes of increasing natural isotope content if desired, for the purpose of tracking and recording the signal generation of the mass spectrometer for multiples of otherwise identical (pre-spike) samples. Given this context, it is easy to see why the present invention works, always, at 20% inclusion of natural-abundance isotope in an admixed natural-abundance isotope/enriched isotope combination spike, but can also be run at increasing natural-abundance isotope percentage inclusions (relative to isotopically enriched spike fraction) in successive spiked analysis—to optimize signal generation empirically. In other words—including 20% natural-abundance isotope in the present molecular amplification spike will always be beneficial—very beneficial!—and it is well within the skill of the art to generate calibration curves therefrom that might identify analytes with that additional amount of natural-abundance isotope inclusion, thus giving results that are even better! This is not a speculative proposition in any way. Once one knows that the key to this technology is to include SOME (20%) natural isotope in what would have previously been an enriched isotope spike but is now an admixed natural-abundance isotope/enriched isotope spike, the incidental "tweaking" that takes place when optional addition of more natural isotope occurs is a matter of routineering. This is why it is possible that up to 90% natural-abundance isotope/10% enriched isotope can be combined in the present molecular amplification spike—because without any trial and error at all, such spikes do often work. Having said all that—20% inclusion of natural isotope, in a combined natural-abundance/enriched isotope spike, is the key to the present invention, and works for all molecules, compositions, compounds and elements of interest—when the analyte of interest is prepared and isolated in a combined spike containing 20% of it in its natural isotopic form and the balance of it in its enriched isotopic form. In lay terms, the present molecular amplification spike—when added to a sample to be analyzed by mass spectrometry—"pulls up out of the weeds" a signal that would otherwise languish beneath the data-to-noise ratio of the spectrometer, and in doing so both identifies and facilitates quantification the substance or analyte sought for.

Additional information regarding the known, prior art preparation and wielding of isotopic spikes, generally, may be found in the inventors' own prior patents, such as those incorporated by reference above. However, the techniques of using a spike—in mass spectrometry—really are as simple as they sound, once one knows what they are and how to apply them. In the most direct terms, when a mass spectrometry sample is prepared, in order to add a spike one simply chooses to add (say) on the order of 10 ppm or 100 ppm as a specific example for the above GSSG on the Agilent Model 6460 mass spectrometer of the spike material to the sample, keeping track of the quantity of spike added (and, in this case, the ratio of natural isotopic abundance of the sample to isotopically enriched isotopes in the spike). Using standard IDMS techniques thereafter, and observing the expected isotopic shifts ubiquitous in nature, calculation of the initial presence and quantity of the same substance as also appears as the natural isotope spike component is a straightforward calculation. More particularly, when a 10 microliter sample is to be analyzed, the amount of added, pre-admixed spike will be between 70-100 picograms (pg), regardless of whether the 10 microliter sample is in liquid form or has been dried after collection and when analyzed using an ESI-QQQ-MS mass spectrometer known in the art. A 70 picogram quantity of spike is used when the substance of interest in a 10 microliter sample is suspected to be present at a level of about 1 nanogram or less. If the substance of interest in the sample is suspected to be present at a level of less than 0.1 nanogram, a 100 picogram addition of the admixed spike (of the present invention) is added to the sample, again for the exemplary ESI-QQQ-MS. The spike can be added directly to the sample or can be pre-fixed to a sample collection device, such as a card, tube or any other sample collection vessel or vehicle. The present inventors have been able to establish, repeatedly, that substances which are undetectable, and certainly unquantifiable, by prior art mass spectrometry—may be both detected AND quantified when the admix spike, at the disclosed addition amounts, are added to the sample and allowed to equilibrate prior to analysis. Equilibration can occur in as little as one minute; as a practical matter samples are allowed to equilibrate for at least thirty minutes to an hour prior to mass spectrometry analysis. Equilibration is generally performed at ambient temperature and pressure. When the present collection media (cards, matrices, tubes for liquids, etc.) are pre-spiked with the admixed spike of the present invention, and the sample to be tested is collected in them or on them, equilibration of the sample naturally occurs during the normal transit time of the sample to the laboratory.

The above describes how important the present technology is, in general terms. However, there are particular applications in which the present technology is literally irreplaceable. One such milieu is the Food and Drug Administration's (FDA's) demand for high precision and low percentage errors, as to measurements of small amounts of materials, and the ability of the present invention to deliver measurements within FDA's requirements. Specifically, the FDA requires accuracy and precision at or below 15% error at the 95% confidence limit. Not only does the U.S. FDA envisions a wide-range of biomarker applications in drug development and actively encourages use of biomarkers in biomedicine, it "has no mercy" for measurements—as to biomarkers or anything else—that do not comply with its error specifications. As a single example among many, when the present technology is used to identify and to quantify the important biomarker GSSG (a glutathione variant of diagnostic and prognostic importance) the present technology has been able (empirically) to achieve percentage error reduction from between 130% to 231% as compared to prior art methods of quantifying GSSG and specifically on the example mass spectrometer FDA accuracy and precision of less than 15% was maintained for one and one half orders of magnitude below the LOQ of that mass spectrometer with all other conditions remaining the same.

Another area of innovation dependent on the present invention is that of lysozyme storage disease diagnosis and treatment. Currently, there are more than fifty known lysozyme storage diseases (LSDs) that tens of thousands of people—who are deficient of one enzyme or another. On the average, these patients die before reaching the age of thirty. Finding a cure for these diseases and effective treatment requires the ability to quantify the presence of the supplemented enzyme, which is generally effective at levels too low to quantify by prior diagnostic methods, and which cannot be dosed at high levels in any case. With enzymes' being proteins, of course, the present technology is perfect for quantifying enzyme levels, especially at their very low levels in the Cerebral Spinal Fluids (CSF) using a corresponding spike that contains the natural-abundance isotope of the enzyme being sought, admixed with an isotopically enriched version of the same enzyme.

Because the present invention is so capable of identifying, and quantifying low levels of substances sought, by definition, the present techniques can achieve quantification in even very tiny samples compared to prior art identification techniques. In a typical blood draw, for example, a phlebotomist might draw two to four standard tubes containing 6-10 ml of patient blood each. Four tubes containing up to 40 ml of blood therefore together constitute a significant mass and volume, presenting shipment, shelf stability and biohazard type challenges among others, for transport. By contrast, the present techniques can easily analyze a blood sample of between 10-30 microliters, including a dried blood spot of 10-30 microliters deposited, and stabilized by simple drying, on a cellulosic fiber, polymer or other inert solid matrix carrier of any type. A typical card of this nature could have four loci for four dried blood spots, inoculated with 10-30 microliters of blood each (from a simple finger "stick"). Indeed, the ability of a mass spectrometer to analyze samples presented on a solid matrix is already well known, see for example U.S. Pat. No. 8,383,420 identified above and incorporated herein by reference. In remote locations or where biological transport presents challenges, cards with dried blood spots or otherwise similarly deposited and desiccated samples including but not limited to biological samples become extremely practical and low-cost sample collection devices with nearly endless applicability in all corners of the globe. Indeed, from a cost management standpoint alone, the cost differential between shipping blood collection tubes versus literally mailing (if necessary) a card with blood spots on it—illustrates how the present technology saves orders of magnitude of shipping costs and complications in sample collection, prior to analysis.

As referenced above, a typical card with dried blood spots will usually contain four blood spots, easily collected from an animal or human patient with a single "finger stick" with a lancet known in the art. The card or matrix may literally be ordinary cellulose, or can be a pure cellulose matrix such as "Whatman paper," or any other inert polymer or composite card with which the biological sample does not react, and on which the biological sample (including but not limited to blood) can dry without deterioration. Cellulosic fibers, cards or solid matrices of this type may be used to collect, store and transport not only blood but other substances, including but not limited to urine, plasma, saliva, bone marrow, cerebral spinal fluid, or any other desiccatable biological, environmental or industrial material including but not limited to water, oil or gas resources, industrial fluids, and other extant substances of interest. Typically, a card contains four pre-assigned loci for four spots of sample, with each spot being able to accommodate about 10-30 microliters of sample prior to desiccation and transport. When it is time to analyze the spots on the card or another matrix by the mass spectrometer, a typical protocol includes the following additional steps. If the collection card or matrix was not pre-treated with the molecular amplification spike of the present invention, a quantity of between 70-100 picograms of the pre-admixed inventive molecular amplification spike is added overtop each blood or specimen spot on the card and allowed to equilibrate. (If the card is pretreated, it is pretreated with the same amount of the pre-admixed inventive spike.) Equilibration means quiet incubation at ambient temperature for at least a minute or a few minutes, or up to an hour or 24 hours or more. After incubation, typically each blood or specimen spot is excised from its carrier with an 8 mm punch tool (8 mm diameter) and each excised blood or specimen spot is then further cut, typically, into four separate pieces. The pieces are typically placed in a microcentrifuge tube containing 70% water and 30% acetonitrile (extraction medium), and the tube is typically vortexed and sonicated at 60 degrees F. for one hour. The sonicated samples are centrifuged and the liquid layer is transferred to a new microcentrifuge tube. Samples in the new tubes are dried on the "SpeedVac" (known in the art) for three hours to yield a pellet sample. The pellets are then reconstituted and analyzed by mass spectrometry according to known protocols, and the results are integrated and used for quantification. In ubiquitous fashion, for molecules (including but not limited to drugs, proteins and enzymes), composition, compounds and elements, analyses conducted as described above is able to identify and quantify substances, in samples, that cannot be quantified without the addition of the admixed "molecular amplification spike," METASPIKE™, of the present invention.

Generally, the present invention does not work efficiently (that is, as accurately or precisely) if it is applied to try to discern and quantify beyond 2 orders of magnitude (quantification improvement range) below the previous Lower Limit of Quantification (LLOQ) of the currently available mass spectrometer. In broad terms, then, the present invention is suitable for identifying and quantifying substances, in a sample, which are present in a 10 microliter sample at between 0.01 and 1 nanograms. Other technologies are suitable for quantifying substances that are present in greater amounts than 1 nanogram per 10 microliter sample, and to the present inventors' knowledge there is currently no technology that will quantify substances that are present in an amount smaller than 0.01 nanograms per 10 microliter sample. So, as a nonlimiting example for MMA, usually present in human blood at around 1.9 micrograms per gram (ranging from 0.0 to 0.35 micrograms per gram) the signal loss from liquid blood to dried blood spots is about a factor of five, meaning that it would not be possible to quantify methylmalonic acid from a 10 microliter dried blood spot without a corresponding methylmalonic pre-admixed natural-abundance/isotope enriched spike to add to the blood spot, in effect to amplify the methylmalonic signal. This is important and representative for any other substance assessed according to the present invention, present in the range of concentration similar to those of GSH, GSSG and MMA. We have achieved less than or equal to 15% error at the 95% confidence limit in our data that meets US FDA (Food and Drug Administration) criteria—whereas, without the present molecular amplification spike, complying this error limitation level would be impossible. Just because this specification mentions MMA and GSSG, however, the invention must not be understood to be limited to any particular substance quantification. The present invention can quantify literally any low concentration indicator metabolite consequential to, say, cancer chemotherapy, by identifying it in its incipient low levels before the chemotherapy patient experiences the discernable negative effects such an indicator portends. It is just as important to find lead, mercury and arsenic in patient and environmental samples as it is to find biological markers in diagnostic samples, and the present invention allows quantification of small amounts of ALL of these important—and often otherwise hidden—molecules, compositions, compounds and elements.

Having said all that, is there any limitation as to a substance that can be a candidate to be quantified by the present use of a molecular amplification spike, that is, as to what the substance can be, within the intact operation of this invention? As described throughout this specification, the invention applies to all molecules, compositions, compounds and elements. By "molecules, compositions, compounds and elements," it is meant, without limitation, biologically active agents, peptides, proteins, enzymes, vitamins, drug metabolites, elements, organic solvents, pesticides, anesthetics, lipids, saccharides, polysaccharides, growth factors, biological markers, antigens, antibodies, growth factor receptors and antigen receptor markers. All of these substances are susceptible of equilibration with its isotopically enriched analogue, and so each of them can be quantified according to the invention using a "spike" that contains both the natural-abundance isotope (of the substance to be measured in a sample) pre-admixed with an isotopically enriched version of the same substance for the purposes of molecular signal amplification. Such pre-mixed molecular amplification spikes, containing as described above 20% natural isotope, can be used to identify and quantify corresponding substances in a sample, when those substances are present in the same in an amount between 0.01-1 nanograms in a 10 microliter sample. For those who are unaccustomed to IDMS and related technologies, it is important to remember that the current isotopically enriched species are not radioactive isotopes. The point of isotope enrichment in preparing the pre-admixed spike is to provide combined natural-abundance/enriched isotope admixtures of virtually anything for which quantification is desired. The present invention is therefore suitable for searching out, discovering and quantifying, literally any substance of interest that might be present, in any sort of sample, in the amount of 0.01 to 0 nanograms in a 10 microliter sample.

While particular amounts of spike have been disclosed in various contexts above (in terms of ppm or picograms) knowing how much (what amount) of spike to use in various isotope dilution mass spectrometry iterations is well within the skill of the art. The present invention inheres in the type of preadmixed spike to be used to give new and necessary quantification results in quantifying low levels of analytes, but those skilled in the art will in turn know how much to use in any given application. Optimizing spike ratios for wielding prior art techniques, associated with isotopically enriched spike technology are well known at this writing, and typically deploy error propagation factors understood by those skilled in the art. Indeed, one virtually never performs the prior art IDMS (or Speciated Isotope Dilution Mass Spectrometry) without the use of error propagation factors. These same ratios, amounts and error propagation factors are equally applicable to the present invention, except that the present molecular amplification spike contains 20% of the naturally occurring isotope of the suspected analyte, as well as the balance isotopically enriched isotope, in contrast to the 100% isotopically enriched isotope(s) present in the IDMS and SIDMS spikes of the prior art. After one knows to add 20% naturally occurring isotope, to the balance of isotopically enriched species, in the present spike material, one skilled in the art already knows how much spike to add to how much sample in order to conduct the necessary mass spectrometry analysis according to the invention. Another way to understand the concept of this paragraph is—the present molecular amplification spike is not a quantification method in and of itself. Instead, the inventive molecular amplification spike is exactly what it says it is—an amplifier of signal which in turn facilitates analysis by IDMS, SIDMS, and (when the signal is amplified enough) calibration curves known in the mass spectrometry art.

The present invention may be used with any existing or after-aquired mass spectrometer or ionization method, including but not limited by a quadrupole, triple quadruple, time of flight, trap mass spectrometer, orbitrap mass spectrometer, sector mass spectrometer or any mass spectrometer using any ionization source such as electrospray, elector ionization, thermal ionization, matrix assisted laser desorption ionization, laser ablation, inductively coupled plasma, or any ionization.

Although the invention has been described with particularity in the foregoing description, the invention is only to be limited insofar as is set forth in the accompanying claims.

We claim:

1. A method for amplifying the mass spectrometry signal of a substance believed to be present below the Lower Limit of Quantification in a sample to be analyzed, comprising the steps of:
   (a) obtaining a quantity of a natural-abundance isotope of a substance of interest;
   (b) obtaining a quantity of an enriched isotope of said same substance of interest;
   (c) admixing 20% of said quantity of a natural-abundance isotope from step (a) with remainder enriched isotope from step (b) to make an admixed molecular amplification spike;
   (d) admixing an aliquot of said molecular amplification spike with a quantity of a sample to be analyzed to create a spiked sample,
   (e) equilibrating said spiked sample for at least one minute to yield an equilibrated sample; and
   (f) analyzing said equilibrated sample by mass spectrometry to quantify an amount of said substance of interest if present.

2. The method according to claim 1, wherein said quantity of a sample in step (d) is an amount between 10 and 30 microliters of human or animal fluid, measured prior to drying, on a blood card and said substance of interest is selected from the group consisting of biologically active agents, peptides, proteins, enzymes, vitamins, drug metabolites, elements, organic solvents, pesticides, anesthetics, lipids, saccharides, polysaccharides, growth factors, biological markers, antigens, antibodies, growth factor receptors and antigen receptor markers.

3. The method according to claim 1, wherein said molecular amplification spike contains between 20 and 90% natural isotope of said substance of interest.

4. The method according to claim 1, wherein the mass spectrometer is a quadrupole, triple quadrupole, time of flight, trap mass spectrometer, orbitrap mass spectrometer, sector mass spectrometer or any mass spectrometer using any ionization source such as electrospray, electron ionization, thermal ionization, matrix assisted laser desorption ionization, laser ablation, inductively coupled plasma, or any ionization.

5. The method according to claim 3, wherein when said quantity of a sample in step (d) is 10 microliters, a quantity of said admixed molecular amplification spike added to said sample is between 70-100 picograms when said sample is dried blood and when the mass spectrometer is an ESI-QQQ-MS mass spectrometer.

6. The method according to claim 1 wherein said sample is selected from the group consisting of whole blood, serum, urine, cerebral spinal fluid or body fluid.

7. The method according to claim 1 wherein said sample is a blood sample which is collected onto, and dried in situ, on an inert solid matrix which has been pre-treated with aliquots of said molecular amplification spike, or an inert solid matrix to which a premixed sample and metaspike have been added and dried in situ.

8. The method according to claim 1, wherein said sample, after equilibration with said molecular amplification spike, may be analyzed in any form of dried, liquid or gaseous.

9. The method according to claim 1, using metaspike to quantify below the LLOQ of a massspectrometer where IDMS and or SIDMS without metaspike would fail to achieve a viable ratio enabling IDMS and or SIDMS with accuracy and precision at or below 15% error at the 95% confidence limit.

10. A molecular amplification spike material, comprising 20% naturally occurring isotope of an analyte of interest, balance isotopically enriched isotope of the same analyte of interest, in premixed form.

* * * * *